United States Patent
Sunkara et al.

(10) Patent No.: US 11,591,226 B1
(45) Date of Patent: Feb. 28, 2023

(54) PLASMA ASSISTED DISTRIBUTED CHEMICAL PRODUCTION

(71) Applicant: Advanced Energy Materials, LLC, Louisville, KY (US)

(72) Inventors: Mahendra Sunkara, Louisville, KY (US); Sivakumar Vasireddy, Louisville, KY (US); Vivekanand Kumar, Louisville, KY (US); Juan He, Louisville, KY (US); Tu Nguyen, Louisville, KY (US); Veerendra Atla, Louisville, KY (US)

(73) Assignee: Advanced Energy Materials, LLC, Louisville, KS (US)

( * ) Notice: Subject to any disclaimer, the term of this patent is extended or adjusted under 35 U.S.C. 154(b) by 0 days.

(21) Appl. No.: 17/411,023

(22) Filed: Aug. 24, 2021

Related U.S. Application Data (60) Provisional application No. 63/070,197, filed on Aug. 25, 2020.

(51) Int. Cl.
*C01B 32/40* (2017.01)
*C07C 1/12* (2006.01)
*C01B 3/04* (2006.01)

(52) U.S. Cl.
CPC ............... *C01B 32/40* (2017.08); *C01B 3/04* (2013.01); *C07C 1/12* (2013.01);
(Continued)

(58) Field of Classification Search
CPC ..... C01B 32/40; C01B 3/04; C01B 2203/061; C01B 2203/0861; C01B 2203/1076; C07C 1/12; C07C 2523/80; C07C 2521/06
See application file for complete search history.

(56) References Cited

U.S. PATENT DOCUMENTS

| 6,471,932 B1 | 10/2002 | Gieshoff et al. |
| 8,288,446 B2 | 10/2012 | Mamedov et al. |

(Continued)

FOREIGN PATENT DOCUMENTS

| EP | 3050865 B1 | 2/2021 |
| WO | 2009126229 A2 | 10/2009 |

OTHER PUBLICATIONS

Iliuta et al., enhanced methanol synthesis process via an integrated process involving CO2 hydrogenation under plasma conditions, (Industrial & Engineering Chemistry Research, published Oct. 22, 2019, 6815-6827).*

(Continued)

*Primary Examiner* — Jafar F Parsa
(74) *Attorney, Agent, or Firm* — Law Office of J. L. Simunic; Joan Simunic (57) ABSTRACT

The present development is a process to produce commodity chemicals such as methanol and syngas using an integrated plasma catalysis technology. The method comprises providing a fixed or fluidized bed reactor having a microwave plasma flame and a catalyst bed with a catalyst, wherein the catalyst is an alloyed bimetallic nanowire. In the process, the plasma flame fluidizes the catalyst thereby producing a more effective catalyst than the non-fluidized catalyst. It is anticipated that the reactor can have a throughput capacity of up to 30 Lpm/kW and can be effective for the conversion of $CO_2$, $CH_4$, air, water, and combinations thereof, through reactions such as pure $CO_2$ splitting, reverse water gas shift (RWGS) for CO production, methanol synthesis, and plasma reforming of methane, thereby making a system that would be attractive for small GTL units.

20 Claims, 3 Drawing Sheets

(52) U.S. Cl.
CPC .. *C01B 2203/061* (2013.01); *C01B 2203/062* (2013.01); *C01B 2203/0861* (2013.01); *C01B 2203/1076* (2013.01); *C01B 2203/1082* (2013.01); *C01B 2203/148* (2013.01); *C07C 2521/06* (2013.01); *C07C 2523/80* (2013.01)

(56) References Cited

U.S. PATENT DOCUMENTS

| | | | |
|---|---|---|---|
| 8,779,215 | B2 | 7/2014 | Kharas |
| 8,809,603 | B2 | 8/2014 | Corradini et al. |
| 9,034,786 | B2 | 5/2015 | Kumar et al. |
| 9,273,020 | B2 | 3/2016 | Schjodt et al. |
| 9,896,339 | B2 | 2/2018 | D'Souza et al. |
| 9,908,093 | B2 | 3/2018 | Simmons et al. |
| 10,435,801 | B2 | 10/2019 | Lei et al. |
| 10,759,668 | B2 | 9/2020 | Hosono et al. |
| 10,829,384 | B2 | 11/2020 | Younes et al. |
| 10,843,172 | B2 | 11/2020 | Park et al. |
| 10,858,302 | B2 | 12/2020 | Chen et al. |
| 10,894,751 | B2 | 1/2021 | Nyce et al. |
| 10,960,378 | B2 | 3/2021 | Finlay |
| 10,974,969 | B2 | 4/2021 | Hu et al. |
| 11,045,793 | B1 | 6/2021 | Soliman et al. |
| 2011/0158858 | A1 | 6/2011 | Alves Ramalho Gomes |
| 2015/0073188 | A1 | 3/2015 | Floudas et al. |
| 2020/0231455 | A1 | 7/2020 | Beach et al. |

OTHER PUBLICATIONS

Li et al., properties of Cu/ZnO/Al2O3 catalysts modified by titanium additives in synthesis of methanol from syngas using orthogonal experimental design,(Asian Journal of Chemistry, vol. 25, No. 12 (2013), 6795-6801.*
Ajayi BP, Kumari S, Jaramillo-Cabanzo D, Spurgeon J, Jasinski J, Sunkara M,A rapid and scalable method for making mixed metal oxide alloys for enabling accelerated materials discovery, Journal of Materials Research, Jun. 2016, p. 1596-607, 31(11), Cambridge Core.
Ajayi BP, Thapa AK, Cvelbar U, Jasinski JB, Sunkara MK, Atmospheric plasma spray pyrolysis of lithiated nickel-manganese-cobalt oxides for cathodes in lithium ion batteries. Chemical Engineering Science, Dec. 31, 2017, p. 302-10, 174, Science Direct.
Bai S, Shao Q, Wang P, Dai Q, Wang X, Huang X, Highly active and selective hydrogenation of CO2 to ethanol by ordered Pd-Cu nanoparticles, Journal of the American Chemical Society, May 24, 2017, p. 6827-30, 139(20), ACS Publication.
Behrens M, Zander S, Kurr P, Jacobsen N, Senker J, Koch G, Ressler T, Fischer RW, Schlögl R, Performance improvement of nanocatalysts by promoter-induced defects in the support material: methanol synthesis over Cu/ZnO: Al, Journal of the American Chemical Society, Apr. 24, 2013, p. 6061-8, 135(16), ACS Publication.
Collins SE, Delgado JJ, Mira C, Calvino JJ, Bernal S, Chiavassa DL, Baltanás MA, Bonivardi AL, The role of Pd-Ga bimetallic particles in the bifunctional mechanism of selective methanol synthesis via CO2 hydrogenation on a Pd/Ga2O3 catalyst, Journal of catalysis, Aug. 1, 2012, p. 90-8, 292, Science Direct.
Daza YA, Kuhn JN, CO2 conversion by reverse water gas shift catalysis: comparison of catalysts, mechanisms, and their consequences for CO2 conversion to liquid fuels, RSC advances, 2016, p. 49675-91, 6(55), RSC advances.
Duyar MS, Gallo A, Snider JL, Jaramillo TF, Low-pressure methanol synthesis from CO2 over metal-promoted Ni-Ga intermetallic catalysts, Journal of CO2 Utilization,Jul. 1, 2020, p. 39:101151, Science Direct.
Eliasson B, Kogelschatz U, Xue B, Zhou LM, Hydrogenation of carbon dioxide to methanol with a discharge-activated catalyst, Industrial & engineering chemistry research, Aug. 3, 1998, p. 3350-7, 37(8), ACS Publication.
Gupta M, He J, Nguyen T, Petzold F, Fonseca D, Jasinski JB, Sunkara MK, Nanowire catalysts for ultra-deep hydrodesulfurization and aromatic hydrogenation, Applied Catalysis B: Environmental, Jan. 1, 2016, p. 246-54, 180, Science Direct.
Ihara T, Ouro T, Ochiai T, Kiboku M, Iriyama Y, Formation of methanol by microwave-plasma reduction of CO2 with H2O, Bulletin of the Chemical Society of Japan. Jan. 1996 ,p. 241-4, 69(1), CSJ Journals.
Kattel S, Ramírez PJ, Chen JG, Rodriguez JA, Liu P, Active sites for CO2 hydrogenation to methanol on Cu/ZnO catalyst, Science, Mar. 24, 2017, p. 1296-9, 355(6331).
Kumar V, Kim JH, Pendyala C, Chernomordik B, Sunkara MK, Gas-phase, bulk production of metal oxide nanowires and nanoparticles using a microwave plasma jet reactor, The Journal of Physical Chemistry C, Nov. 20, 2008, p. 17750-4, 112(46), ACS Publication.
Li D, Rohani V, Fabry F, Ramaswamy AP, Sennour M, Fulcheri L,Direct conversion of CO2 and CH4 into liquid chemicals by plasma-catalysis, Applied Catalysis B: Environmental, Feb. 1, 2020, 118228, 261, Science Direct.
Luo Z, Tian S, Wang Z, Enhanced activity of Cu/ZnO/C catalysts prepared by cold plasma for CO2 hydrogenation to methanol, Industrial & Engineering Chemistry Research, Mar. 2, 2020, p. 5657-63, 59(13), ACS Publication.
Marcos FC, Lin L, Betancourt LE, Senanayake SD, Rodriguez JA, Assaf JM, Giudici R, Assaf EM, Insights into the methanol synthesis mechanism via CO2 hydrogenation over Cu—ZnO—ZrO2 catalysts: Effects of surfactant/Cu—Zn—Zr molar ratio, Journal of CO2 Utilization, Oct. 1, 2020 ,p. 01215, 41, Science Direct.
Medrano-García JD, Ruiz-Femenia R, Caballero JA, Optimal carbon dioxide and hydrogen utilization in carbon monoxide production, Journal of CO2 Utilization, Dec. 1, 2020, p. 215-30, 34, Science Direct.
Nambo A, He J, Nguyen TQ, Atla V, Druffel T, Sunkara M, Ultrafast carbon dioxide sorption kinetics using lithium silicate nanowires, Nano letters, Jun. 14, 2017, p. 3327-33, 17(6), ACS Publication.
Neyts EC, Ostrikov K, Sunkara MK, Bogaerts A, Plasma catalysis: synergistic effects at the nanoscale, Chemical reviews, Dec. 23, 2015, p. 13408-46, 115(24), ACS Publication.
Nguyen TQ, Atla V, Vendra VK, Thapa AK, Jasinski JB, Druffel TL, Sunkara MK, Scalable solvo-plasma production of porous tin oxide nanowires, Chemical Engineering Science, Nov. 2, 2016, p. 20-26, 154, Science Direct.
Olah GA, Goeppert A, Czaun M, Prakash GS, Bi-reforming of methane from any source with steam and carbon dioxide exclusively to metgas (CO-2H2) for methanol and hydrocarbon synthesis, Journal of the American Chemical Society, Jan. 16, 2013, p. 648-50,135(2), ACS Publication.
Pérez-Fortes M, Schöneberger JC, Boulamanti A, Tzimas E. Methanol synthesis using captured CO2 as raw material: Techno-economic and environmental assessment, Applied Energy, Jan. 1, 2016, p. 718-32, 161, Science Direct.
Pedersen JK, Batchelor TA, Bagger A, Rossmeisl J, High-entropy alloys as catalysts for the CO2 and CO reduction reactions, Acs Catalysis, Jan. 13, 2020, p. 2169-76, 10(3), ACS Publication.
Previtali D, Longhi M, Galli F, Di Michele A, Manenti F, Signoretto M, Menegazzo F, Pirola C, Low pressure conversion of CO2 to methanol over Cu/Zn/Al catalysts. The effect of Mg, Ca and Sr as basic promoters, Fuel, Aug. 15, 2020, p. 117804, 274, Science Direct.
Puliyalil H, Jurković DL, Dasireddy VD, Likozar B, A review of plasma-assisted catalytic conversion of gaseous carbon dioxide and methane into value-added platform chemicals and fuels, RSC Advances, 2018, p. 27481-508, 8(48), RCS.
Ronda-Lloret M, Wang Y, Oulego P, Rothenberg G, Tu X, Shiju NR, CO2 hydrogenation at atmospheric pressure and low temperature using plasma-enhanced catalysis over supported cobalt oxide catalysts, ACS sustainable chemistry & engineering, Nov. 17, 2020, p. 17397-407, 8(47), ACS Publication.
Snoeckx R, Bogaerts A, Plasma technology—a novel solution for CO 2 conversion?, Chemical Society Reviews, 2017, p. 5805-63, 46(19), RCS.

(56) References Cited

OTHER PUBLICATIONS

Snoeckx R, Wang W, Zhang X, Cha MS, Bogaerts A, Plasma-based multi-reforming for Gas-To-Liquid: tuning the plasma chemistry towards methanol, Scientific reports, Oct. 29, 2018, p. 1-7, 8(1), Nature.

Studt F, Sharafutdinov I, Abild-Pedersen F, Elkær CF, Hummelshøj JS, Dahl S, Chorkendorff I, Nørskov JK, Discovery of a Ni—Ga catalyst for carbon dioxide reduction to methanol, Nature chemistry, Apr. 2014, p. 320-24, 6(4), Nature.

Sun Y, Li J, Chen P, Wang B, Wu J, Fu M, Chen L, Ye D, Reverse water-gas shift in a packed bed DBD reactor: Investigation of metal-support interface towards a better understanding of plasma catalysis, Applied Catalysis A: General, Feb. 5, 2020, p. 117407, 591, Science Direct.

Wang L, Yl Y, Guo H, Tu X, Atmospheric pressure and room temperature synthesis of methanol through plasma-catalytic hydrogenation of CO2,ACS Catalysis, Jan. 5, 2018, p. 90-100, 8(1), ACS Publication.

Whitehead JC, Plasma-catalysis: the known knowns, the known unknowns and the unknown unknowns, Journal of Physics D: Applied Physics, May 12, 2016,p. 243001, 49(24), IOP Science.

Wu C, Lin L, Liu J, Zhang J, Zhang F, Zhou T, Rui N, Yao S, Deng Y, Yang F, Xu W,Inverse ZrO2/Cu as a highly efficient methanol synthesis catalyst from CO2 hydrogenation, Nature communications, Nov. 13, 2020 , p. 1-0, 11 (1), Nature.

Zhang X, Han S, Zhu B, Zhang G, Li X, Gao Y, Wu Z, Yang B, Liu Y, Baaziz W, Ersen O,Reversible loss of core-shell structure for Ni—Au bimetallic nanoparticles during CO2 hydrogenation, Nature Catalysis, Apr. 2020,p. 411-7, 3(4), Nature.

\* cited by examiner

PLASMA ASSISTED DISTRIBUTED CHEMICAL PRODUCTION

CROSS-REFERENCE TO PRIOR APPLICATIONS

The present application claims priority to previously filed U.S. Patent Application 63/070,197, incorporated herein in its entirety by reference.

GOVERNMENT INTEREST

This invention was made with government support under DE-SC0019939 awarded by the U.S. Department of Energy. The government has certain rights in the invention.

FIELD OF THE INVENTION

The invention relates to a method of processing air, carbon dioxide, water, and methane into value-added compounds in mini-plant processing units.

BACKGROUND OF THE INVENTION

Carbon dioxide ($CO_2$) is a major contributor to greenhouse gases. However, $CO_2$ can also be a rich carbon source that can be used in value-added products. For example, one well-known use of $CO_2$ is for the production of synthesis gas or syngas. Syngas is a mixture of carbon monoxide (CO) and hydrogen gas ($H_2$). $CO_2$ can react with decomposed methane ($CH_4$) to generate syngas by the equation $CO_2 + CH_4 \rightarrow 2CO + 2H_2$. Alternatively, $CO_2$ can be split into CO and oxygen by use of, for example, microwave radiation and then the CO can be combined with $H_2$. The resulting CO is the building block of many relevant chemical products, such as methanol and other alcohols, various aldehydes, and metal carbonyls.

The challenge is identifying relatively inexpensive methods to convert $CO_2$ into value-added starting materials that can then be used in known processes for producing value-added products. Traditional conversion facilities can be expensive to build, to operate, and to maintain. One option is to use a small-scale conversion facility. Small gas to liquid conversion (GTL) units that convert natural gas into valuable liquid products have a nominal capacity of 100,000-300,000 standard cubic feet per day (scfd) production, require relatively low capital expenditures, allow for customization with existing processes, provide opportunities for the monetization of flared gas in remote locations, and provide decentralization flexible for production facilities. Further GTL technologies implemented at small scales provide liquid fuel and chemicals with energy content which is easier to handle for storage and transportation, and provide opportunities to reduce energy costs and lessen the dependence on fossil fuels by utilizing wind and/or solar power for operation. Small scale reactors for the conversion of syngas (mixture of CO and $H_2$) to methanol are known in the art. However, no similar systems are known for the conversion of $CO_2$.

The authors believe that small scale GTL reactor units could improve conversion rates and selectivity by using plasma reactors rather than traditional thermal reactors. Plasma reactors normally operate at mild conditions, such as at atmospheric pressure, yet still allow for a range of reaction temperatures depending on the plasma source. Warm plasmas, such as microwave plasma (MW), can simultaneously provide a high degree of non-equilibrium and a high electron density which translates to efficient reactor productivity and selectively and might be very promising for $CO_2$ conversion. However, to maximize efficiency, catalysts designed specifically for use with plasma reactors are needed.

SUMMARY OF THE PRESENT INVENTION

The present development is a process to produce commodity chemicals such as carbon monoxide, methanol and syngas from carbon dioxide using an integrated plasma catalysis technology. The method comprises providing a fixed or fluidized bed reactor having a microwave plasma flame and a catalyst bed with a catalyst, wherein the catalyst is an alloyed bimetallic nanowire. In the process, the plasma flame fluidizes the catalyst thereby producing a more effective catalyst than the non-fluidized catalyst. The catalysts are prepared using Solvo-Plasma oxidation or microwave intensified plasma pyrolysis or impregnation techniques. It is anticipated that the reactor can have a throughput capacity of up to 30 Lpm/kW and can be effective for the conversion of $CO_2$, $CH_4$, air, water, and combinations thereof, through reactions such as pure $CO_2$ splitting, reverse water gas shift (RWGS) for CO production, methanol synthesis, and plasma reforming of methane.

DETAILED DESCRIPTION OF THE PRESENT DEVELOPMENT

The present development is a process to produce commodity chemicals such as carbon monoxide (CO), methanol, and syngas starting with carbon dioxide ($CO_2$) and using an integrated plasma catalysis technology. The method comprises providing a fixed or fluidized bed reactor having a microwave plasma flame and a catalyst bed with a catalyst, wherein the catalyst is an alloyed bimetallic nanowire. In the process, the catalyst is fluidized through the plasma flame for controlling the contact time between the catalyst and plasma flame, thereby improving the synergic effect between plasma excitation of gas phase species and catalytic sites. Without limitation, the integrated plasma catalysis technology has been shown to effectively hydrogenate $CO_2$ to methanol at atmospheric pressure or relatively low pressures relative to traditional conversion technologies. In a preferred embodiment, the system operates at a pressure of less than about 30 bar, and has a throughput of $CO_2$ of from 3 lpm/kW to about 30 lpm/kW.

Figure 1:
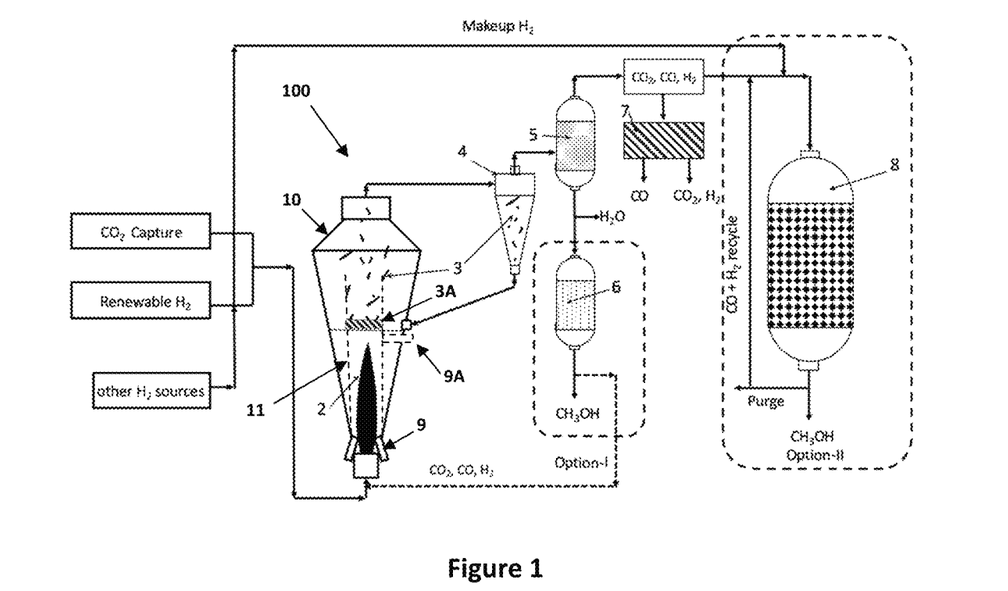
FIG. 1 is a schematic of the reactor system used with the alloyed bimetallic catalyst for the process of the present invention.

A schematic of the integrated plasma catalysis technology system 100 is shown in FIG. 1 and comprises a plasma catalytic reactor 10 having a plasma flame or plasma discharge 2 and a fixed or fluidized catalyst bed 3, a cyclone 4, and at least one condenser 5, 6. Optionally, the system 100 may further include a fixed bed reactor 8 to receive unreacted starting material gases and recycle gases. In a preferred embodiment, the equipment is proportioned to fit within a small GTL production facility. In a preferred embodiment, the plasma catalysis reactor 10 is oriented with the microwave plasma discharge 2 vertically upwards to maximize the residence time and enhance the fluidization of the catalyst.

The present development uses a microwave plasma flame, which is a non-thermal plasma flame. As is known in the art, electromagnetic microwave (MW) energy is produced using a magnetron, the MW energy is transferred to a hollow coaxial electrode using waveguides or structures for guiding electromagnetic waves, then the microwave energy is coupled into a plasma gas to generate the microwave plasma. Optionally, the MW energy may pass through an isolator and/or a precision power dectector and/or a microwave matching unit before entering the waveguide. In the present development, the microwave energy is produced with a 3 kW magnetron head, then passes through an isolator, and then through an MKS Precision Power Detector, and then through a SmartMatch® AX3060, before entering a tapered waveguide with provisions for a circular hole of 2-inch diameter for supporting a quartz tube 11 that confines the microwave plasma discharge. Tapering the waveguide allows for concentrating the electric field density, which is produced by the magnetron and is directed at the waveguide end through WR284 channels. In the present development, the waveguide is positioned under the plasma source.

A reactor suitable for the present development is disclosed in US 2019/0193044. Referring again to FIG. 1, the reactor 10 is designed with gas inlet ports 9 at the bottom. The gas inlet ports 9 allow for entry of sheath gas and plasma forming gas. In a preferred embodiment, the sheath gas is introduced tangentially and the plasma forming gas is introduced at a 30-deg angle relative to the middle of the quartz tube. As is known in the art, sheath gases, such as argon or nitrogen, are added to minimize the radiation heat losses due to their low thermal conductivity values and the sheath gases help keep the quartz tube safe from melting. In an exemplary embodiment, a 1.5-inch diameter quartz tube is used as the dielectric medium to confine the plasma discharge, which allows for optimum residence time and flexibility for handling higher gases flow rates, and to support the catalyst bed 3A. In a preferred embodiment, the quartz tube includes at least one gas inlet 9A located between the plasma flame 2 and the catalyst bed 3A. Optionally, the reactor 10 may further include one or more gas sampling ports (not shown). The catalyst bed 3A rests on an Inconel mesh screen secured within the quartz tube. The catalyst bed 3A is placed directly above the plasma discharge 2 in adiabatic fashion such that heat generated by plasma excitation of molecules will be transferred to catalyst and no external heat is required making the process energy efficient. Optionally, the catalyst bed position can be varied in the discharge area to optimize the plasma catalytic processes.

The catalysts of the present development are bimetallic alloy nanowires or bimetallic nanoparticle supported metal oxide nanowires. Bimetallic nanowires are formed with a reaction between a catalytically active metal containing precursor with a metal oxide nanowire under reaction conditions that cause the catalyst components to alloy, thereby created a new alloyed bimetallic catalyst. The inventors have found inert or vacuum annealing technique under either thermal or plasma discharge conditions to be effective for the alloying process. Bimetallic alloy nanoparticle supported metal oxide nanowires are formed with reaction of catalytic metal containing precursors under plasma oxidation conditions.

The inventors have also surprisingly found that when the alloyed bimetallic catalysts are used in the plasma discharge reactor system, there is a surprising synergistic effect observed between the microwave plasma and the catalyst. Specifically, the alloyed catalysts have been found to be effective for $CO_2$ conversion under mild reaction conditions. For example, the alloyed catalysts effectively convert $CO_2$ at reaction pressures below 7 bar, and as low as 1 torr, with the plasma power at from 3 lpm/kW to 30 lpm/kW.

Alloyed Catalyst Synthesis: The bimetallic nanowire-based catalysts are selected from alloyed nanowire compositions (a) copper-zinc elements alloyed into titanium oxide nanowires ($Cu_xZn_{1-x}TiO_2$ NWs, wherein x=1-20), (b) copper element alloyed into titanium oxide nanowires ($Cu_xTi_{1-x}O_2$, wherein x=1-18), (c) nickel alloyed into zinc oxide nanowires ($Ni_xZn_{1-x}O_2$, wherein x=1-20), (d) nickel alloyed into titanium oxide nanowires ($Ni_xTi_{1-x}O_2$, wherein x=1-10), and (e) iron alloyed into aluminum oxide nanowires ($Fe_xAl_{2-x}O_3$, wherein x=1-20); or from supported nanowire compositions (f) copper-zinc bimetallics on zinc oxide, (g) copper zinc bimetallics on titanium oxide, (h) copper-gallium supported on titanium oxide nanowires, (i) nickel-gallium bimetallics on titanium oxide nanowires. Optionally, the supported catalysts can use zinc oxide, titanium oxide or alumina nanowires.

The plasma oxidation technique is performed by mixing the metal oxide nanowires with a liquid metal precursor of the catalytically-active metals to create a paste, and then spreading the paste on a quartz substrate, and then exposing the paste to a vertical microwave plasma discharge at atmospheric conditions for a predetermined period of time. The liquid metal precursor may comprise one or more metal precursors. When a combination of metal precursors is used, the metals co-impregnated as mixed metal alloy oxide nanoparticles onto the nanowire support. The plasma oxidation technique produces mixed metal oxide nanoparticles on the nanowire surface. In a preferred embodiment, the plasma flame conditions are as follows: sheath gas is argon with a flow rate of 8 lpm, plasma gas is air with a flow rate of 10 lpm, the plasma power is 800 W-1000 W, and the exposure time is from about 30 seconds to about 1 minute.

The vacuum annealing technique is performed by mixing the metal oxide nanowires with an aqueous solution of the metal precursor of the catalytically-active metals to create a paste, and then spreading the paste on a quartz or alumina substrate, and then drying the paste at from about 120° C. to about 130° C. at 1 atmosphere pressure, and then placing the paste-coated substrate in a vacuum or inert atmosphere chamber for a predetermined period of time. The preferred reaction conditions for preparation of the copper-zinc catalysts of the present development are to maintain the vacuum chamber at temperatures below 750° C., and more preferably at temperatures of from about 150° C. to about 550° C., with an exposure or operating time of from about 2 hours to about 6 hours per cycle. Each cycle results in from about 2 wt % to about 10 wt % metal alloying. If desired, multiple cycles may be performed, and it is recommended that the vacuum chamber be purged between cycles with a purge gas, such as nitrogen, helium or argon, to maintain an oxygen lean environment. Further vacuum or inert annealing conditions include maintaining a nitrogen gas flow rate of about 50 sccm and a vacuum pressure of from about 1 torr to about 760 torr.

Figure 3:
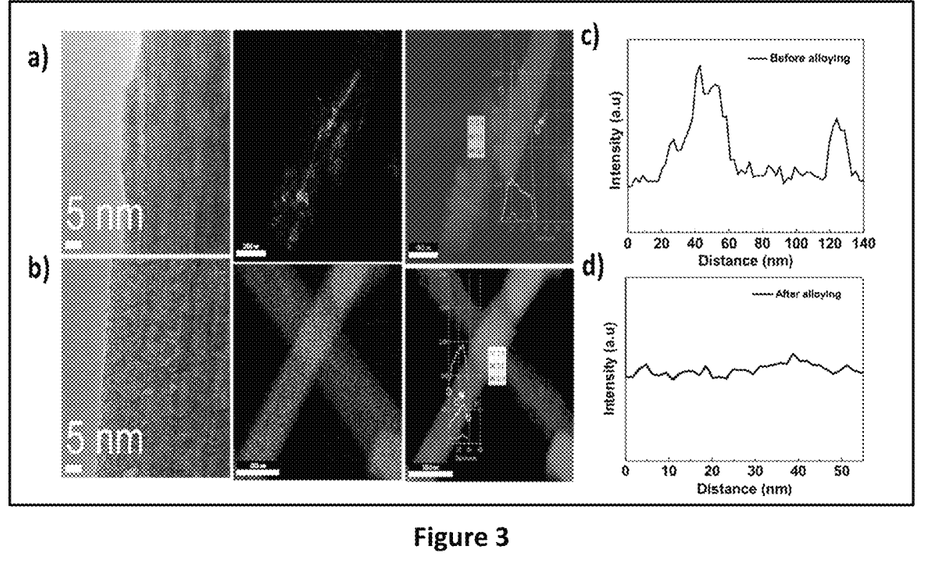
FIG. 3 is a set of TEM images of a copper titania nanowire shown (a) before the alloying process and (b) after the alloying process, with TEM EDX line profile scan analyses shown for the catalyst (c) before the alloying process and (d) after the alloying process; and, FIG. 4 is a set of optical photographs of catalysts before and after exposure to plasma catalysis reactions, wherein the top images show $Cu_xTi_{1-x}O_y$ nanowire based catalysts before and after exposure to plasma catalytic process for one hour indicating no change in the appearance and stability, and wherein the bottom images show Cu particle supported ZnO nanowire based catalysts before and after exposure to plasma catalytic process indicating sintering and change, and wherein FIG. 4 indicates stability of alloyed nanowire based catalysts with exposure to plasma catalytic processes.
Figure 4:
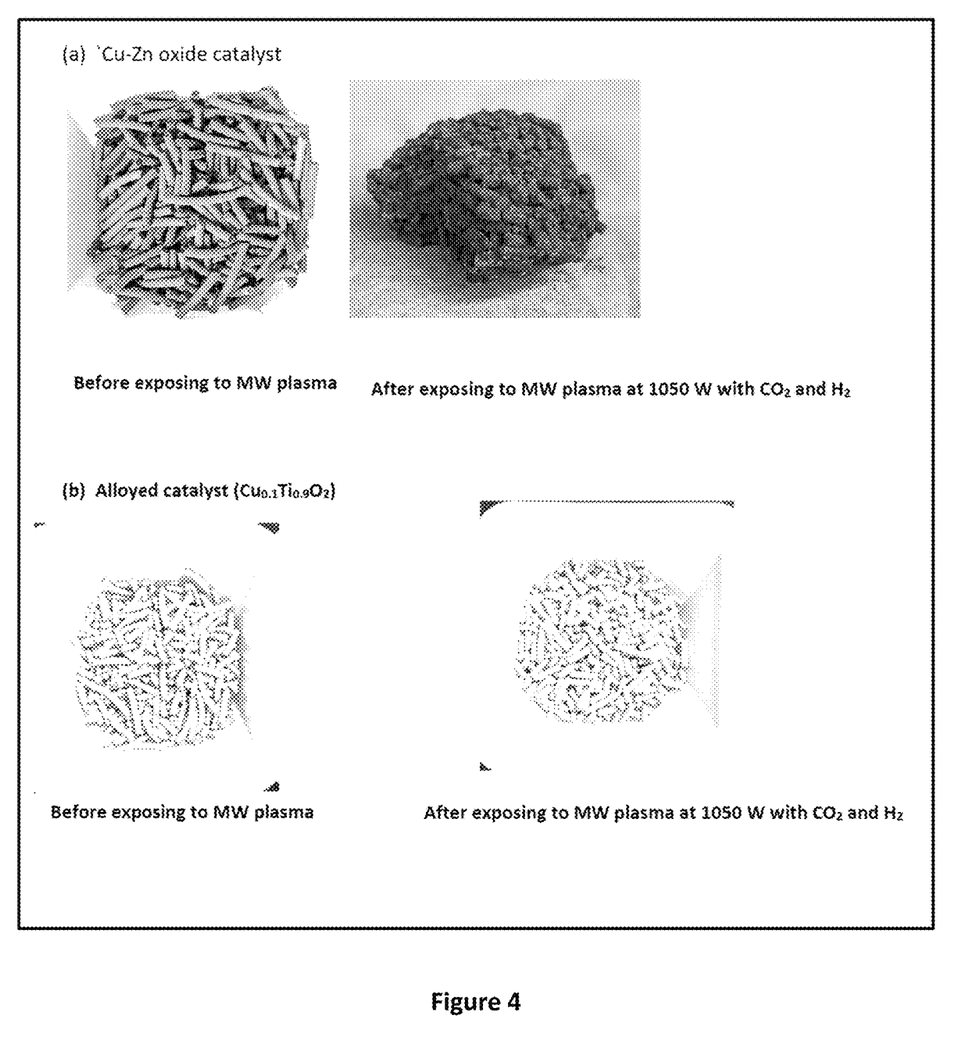

The alloyed bimetallic catalysts have different physical characteristics, such as crystalline surface sites and highly dispersed single atom sites for catalytic alloying elements, as shown by the TEM images and the TEM EDX line profiles for copper alloyed titania nanowires in FIG. 3.

The following examples are presented to better explain the present development, and are not intended to otherwise limit the scope of the claims herein. Any general reference to a specific catalyst composition is intended to apply to all catalyst compositions unless otherwise noted. For example, a detailed catalyst preparation is described for a $Cu_{0.2}Zn_{0.8}O$ supported on $TiO_2$ NWs catalyst, but the preparation method can apply to any composition set forth herein.

For the purpose of the following experiments, the reactor shown in FIG. 1 was loaded with from about 30 g to about 100 g of catalyst. The reactor was operated at atmospheric conditions to generate a highly dense vertical plasma discharge operating at powers ranging from 300 W-3 kW. The plasma was ignited with argon. $CO_2$ and $H_2$ were introduced through the gas inlet ports at flow rates of from about 5 lpm to about 10 lpm while maintaining the plasma discharge. It was observed that microwave plasma discharge volume is almost linearly proportional with applied power. Liquid product was collected from condenser and gas samples were taken from the sampling port.

A catalyst comprising $Cu_{0.2}Zn_{0.8}O$ particles supported on $TiO_2$ NWs is prepared by dissolving predetermined quantities of copper nitrate and zinc nitrate in distilled water to make a precursor solution having predetermined molar proportions. The prepared solution is then used to make a slurry mixed with $TiO_2$ nanowires. The slurry is applied on a substrate as a thick film and exposed to air microwave plasma (800 watt power) for 30 seconds. The dried powder is then extruded in a cylinder shape of 1 mm diameter and 0.25" length using lab scale extruder.

Plasma catalysis for $CO_2$ splitting. A 92% $(Cu_{0.2}Zn_{0.8}O)$/8% gamma-$Al_2O_3$ catalyst was evaluated for $CO_2$ splitting performance. As shown in Table 1, the presence of the catalyst significantly improved the $CO_2$ conversion.

TABLE 1

Summary of conditions used for determining baseline $CO_2$ conversion

| Condition | Power | Flow rates | Ratio | $CO_2$ conversion |
|---|---|---|---|---|
| $CO_2$ only | 500-1200 W | $CO_2$ = 7.5-16 lpm | | 13-27% |
| $CO_2$ and $H_2$ | 450-900 W | $CO_2$: 3-8 lpm, Ar: 5-8 lpm, $H_2$: 3-8 lpm | $CO_2$:$H_2$ = 1 | 53-62% |
| $CO_2$ and $N_2$ | 500-1200 W | $CO_2$: 2-8 lpm, $N_2$ = 5-8 lpm | $CO_2$:$N_2$ = 1 | 22-40% |
| $CO_2$ and $O_2$ | 500 W | $CO_2$: 5-6 lpm, $O_2$ = 0.5-0.6 lpm | $CO_2$:$O_2$ = 10 | 10-11% |
| $CO_2$, $H_2$ and Catalyst | 350-500 W | $CO_2$ = 1.5-11 lpm, Ar = 6-10 lpm, $H_2$ = 4.5-9 lpm, GHSV = 4800 $h^{-1}$ $g_{cat}^{-1}$ | $CO_2$:$H_2$ = 1-3 | 77-93% |

The data collected was then evaluated to show the $CO_2$ conversion as a function of power throughput and specific energy input (SEI) for various conditions and as compared to the prior art, as summarized in Table 2. Using $CO_2$ only, the energy efficiency of pure $CO_2$ splitting as a function of SEI in the inventors' reactor was studied and was found to be comparable to reported literature values.

TABLE 2

Summary of $CO_2$ conversion as a function of power throughput and specific energy input (SEI)

| Condition | Power | $CO_2$ conversion (%) | Lpm/kW | SEI (eV/molecule) |
|---|---|---|---|---|
| $CO_2$ only | 500-1200 W | 24.7 | 6.7 | 2.3 |
| $CO_2$ only | | 20.1 | 10 | 1.5 |
| $CO_2$ only | | 22.7 | 12 | 1.3 |
| $CO_2$ only | | 25.8 | 15 | 1.0 |
| $CO_2$ only | | 13.9 | 16 | 0.9 |
| $CO_2$ only | | 22.2 | 20 | 0.8 |
| $CO_2$ only | | 22 | 24 | 0.6 |
| $CO_2$ only | | 27.1 | 32 | 0.5 |
| $CO_2$ and $H_2$ ($CO_2$:$H_2$ = 1) | 450-900 W | 61.5 | 3.4 | 4.5 |
| $CO_2$ and $H_2$ ($CO_2$:$H_2$ = 1) | | 61.1 | 4.4 | 3.5 |
| $CO_2$ and $H_2$ ($CO_2$:$H_2$ = 1) | | 60.5 | 6.7 | 2.3 |
| $CO_2$ and $H_2$ ($CO_2$:$H_2$ = 1) | | 53.8 | 13.2 | 1.1 |
| $CO_2$ and $H_2$ ($CO_2$:$H_2$ = 1) | | 53.1 | 16.2 | 0.9 |
| $CO_2$ and $N_2$ ($CO_2$:$N_2$ = 1) | 500-1200 W | 39.5 | 2.5 | 6.1 |
| $CO_2$ and $N_2$ ($CO_2$:$N_2$ = 1) | | 35 | 4 | 3.8 |
| $CO_2$ and $N_2$ ($CO_2$:$N_2$ = 1) | | 22.4 | 6.7 | 2.3 |
| $CO_2$ and $N_2$ ($CO_2$:$N_2$ = 1) | | 27.9 | 8 | 1.9 |
| $CO_2$ and $N_2$ ($CO_2$:$N_2$ = 1) | | 24.4 | 10 | 1.5 |
| $CO_2$ and $N_2$ ($CO_2$:$N_2$ = 1) | | 23.5 | 12 | 1.3 |
| $CO_2$ and $N_2$ ($CO_2$:$N_2$ = 1) | | 25.3 | 14.5 | 1.0 |
| $CO_2$ and $O_2$ ($CO_2$:$O_2$ = 10) | 500 W | 11.9 | 16 | 0.9 |
| $CO_2$ and $O_2$ ($CO_2$:$O_2$ = 10) | | 10.4 | 20 | 0.8 |
| $CO_2$, $H_2$ and Catalyst ($CO_2$:$H_2$ = 1-3) | 350-500 W | 93 | 4.3 | 3.5 |
| $CO_2$, $H_2$ and Catalyst ($CO_2$:$H_2$ = 1-3) | | 91 | 5 | 3.0 |
| $CO_2$, $H_2$ and Catalyst ($CO_2$:$H_2$ = 1-3) | | 84.8 | 6.3 | 2.4 |
| $CO_2$, $H_2$ and Catalyst ($CO_2$:$H_2$ = 1-2) | | 86.2 | 11.1 | 1.4 |
| $CO_2$, $H_2$ and Catalyst ($CO_2$:$H_2$ = 1-1) | | 79.5 | 18.5 | 0.8 |
| $CO_2$, $H_2$ and Catalyst ($CO_2$:$H_2$ = 1-1) | | 81.5 | 19.5 | 0.8 |
| $CO_2$, $H_2$ and Catalyst ($CO_2$:$H_2$ = 1-1) | | 77.3 | 24.4 | 0.6 |

Based on the results in Table 2, the inventors have concluded that: (a) plasma catalyst synergy is clearly seen in terms of higher $CO_2$ conversion (77-93%) compared to conversions without the catalyst; (b) pure $CO_2$ conversion is between 13-27% with an energy efficiency between 40-50% and compares reasonably well with reported literature values; (c) $CO_2$ conversion improves significantly (53-62%) when $H_2$ is added to the reactor due to formation of water along with CO production; (d) the power throughput of the inventive MW reactor is very high (up to 30 lpm/kW) and can process large amount of gases with high energy efficiency (up to 77% at higher lpm/kW); and (e) addition of $N_2$ improves the $CO_2$ conversion while addition of $O_2$ seems to suppress the $CO_2$ conversion as has been reported in literature.

$CO_2$ hydrogenation to CO in the presence of catalyst: Using the integrated plasma catalysis technology system 100 with a single condenser set at a temperature of 10° C., $CO_2$ hydrogenation to CO in the presence of a catalyst of the present invention was evaluated. Specifically, Cu—Zn bimetallic alloy catalyst ($Cu_xZn_{1-x}O$) supported on to $TiO_2$ nanowires ($Cu_{0.1}Zn_{0.9}O/TiO_2$ NWs; $Cu_{0.2}Zn_{0.8}O/TiO_2$ NWs) catalysts were used. Reaction conditions were the same as shown in Table 1. As shown in Table 3, when the $Cu_{0.1}Zn_{0.9}O/TiO_2$ NWs catalyst was used, greater than 90% $CO_2$ conversion with 100% selectivity to CO was observed. Similar results were obtained when the $Cu_{0.2}Zn_{0.8}O/TiO_2$ NWs catalyst was used. These results represent a significant improvement over the uncatalyzed reactions and demonstrate that the present process has a high process throughput (10-20 lpm/kW) with an energy efficiency >60%. The results also demonstrate that the non-thermal microwave plasma and the Cu—Zn and Cu—Ti bimetallic alloy catalysts ($Cu_xZn_{1-x}O$, $Cu_xTi_{1-x}O_{2-\delta}$) act in synergy to achieve high $CO_2$ conversion at a 100% selectivity to CO at mild reaction conditions. The inventors also noted that this was an adiabatic reactor operation in which all the energy generated by plasma excitation of species was transferred to catalyst and no external heat needed to be supplied to the catalyst bed.

TABLE 3

Conditions for $CO_2$ hydrogenation experiment

| Catalyst | $CO_2$ Conversion (%) | Selectivity to CO | Total $CO_2$ Lpm/kW | $H_2$/ $CO_2$ |
|---|---|---|---|---|
| $Cu_{0.1}Zn_{0.9}O/TiO_2$ NWs | 93.0 | 100 | 4.3 | 3 |
| $Cu_{0.1}Zn_{0.9}O/TiO_2$ NWs | 91.0 | 100 | 5.0 | 3 |
| $Cu_{0.2}Zn_{0.8}O/TiO_2$ NWs | 84.8 | 100 | 6.3 | 3 |
| $Cu_{0.2}Zn_{0.8}O/TiO_2$ NWs | 86.2 | 100 | 11.1 | 2 |
| $Cu_{0.2}Zn_{0.8}O/TiO_2$ NWs | 81.5 | 100 | 19.5 | 1 |
| $Cu_{0.2}Zn_{0.8}O/TiO_2$ NWs | 79.5 | 100 | 18.5 | 1 |
| $Cu_{0.2}Zn_{0.8}O/TiO_2$ NWs | 77.3 | 100 | 24.4 | 1 |
| $Cu_{0.1}Ti_{0.9}O_2$ NWs | 59.7 | 100 | 12.1 | 1 |
| $Cu_{0.1}Ti_{0.9}O_2$ NWs | 67.7 | 100 | 12.1 | 1.5 |
| $Ni_{0.1}Ti_{0.9}O_2$ NWs | 43.7 | 100 | 12.0 | 1 |
| $Ni_{0.1}Ti_{0.9}O_2$ NWs | 53.9 | 100 | 12.0 | 1.5 |
| 17% $(Cu_{0.2}Ga_{0.8}O)$-83% $TiO_2$ NWs | 58.4 | 100 | 12.0 | 1 |
| 17% $(Cu_{0.2}Ga_{0.8}O)$-83% $TiO_2$ NWs | 71.7 | 100 | 12.0 | 1.5 |
| 17% $(Cu_{0.2}Zr_{0.8}O)$-83% $TiO_2$ NWs | 54.8 | 100 | 12.0 | 1 |
| 17% $(Cu_{0.2}Zr_{0.8}O)$-83% $TiO_2$ NWs | 62.9 | 100 | 12.0 | 1.5 |
| No catalyst ($CO_2$ only) | 24.7 | 100 | 6.7 | n/a |
| No catalyst ($CO_2$ only) | 13.9 | 100 | 16.0 | n/a |
| No catalyst ($CO_2$ only) | 22 | 100 | 24 | n/a |
| $CO_2$ + $H_2$ w/no catalyst | 61.1 | 100 | 4.4 | 1 |
| $CO_2$ + $H_2$ w/no catalyst | 60.5 | 100 | 6.7 | 1 |
| $CO_2$ + $H_2$ w/no catalyst | 53.1 | 100 | 16.2 | 1 |

Figure 2:
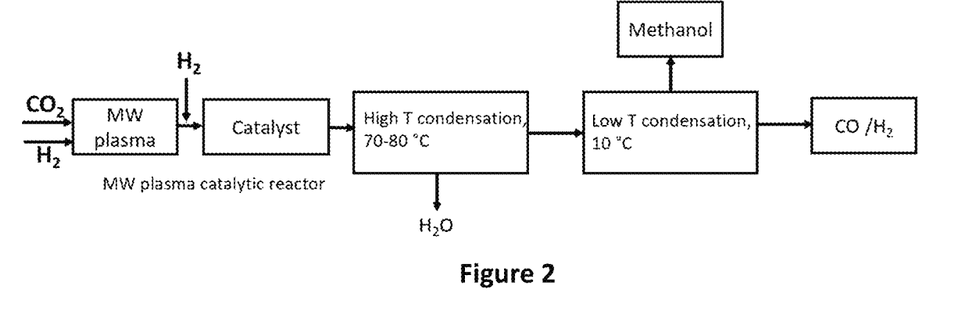
FIG. 2 is a processing scheme for performing the present invention.

$CO_2$ hydrogenation to CO and Methanol: The inventors have found that $CO_2$ hydrogenation results in the production of methanol when $H_2$ is added before the catalyst bed to establish plasma catalytic synergy, as shown in FIG. 2. When the $H_2$ was not added between the plasma discharge and the catalyst bed, essential as no methanol was formed. However, when $H_2$ was added both at the bottom of the reactor and into the reactor just below a fixed catalyst bed using the $Cu_{0.2}Zn_{0.8}O/TiO_2$ NWs catalyst with a $CO_2$/$H_2$-2-3, throughput-10 lpm/kW, and at atmospheric pressure, a methanol yield of 3% with 58% $CO_2$ conversion was observed.

Syngas production through $CO_2$ reforming of $CH_4$ using MW plasma reactor: The economic feasibility of methanol production demands a $H_2$/$CO_2$ ratio of 2-3 and is strongly dependent on the hydrogen cost. In order to look for other ways to produce methanol the inventors have recently carried out experiments for tri-reforming of methane in plasma discharge. This solution (using renewable energy) can be economically more competitive when $CO_2$ emissions are associated with natural gas/shale gas/flare gas, or where natural gas/shale infrastructure or pipeline and renewable energy is available. The produced syngas can then process down further to liquid fuels/chemicals.

Methanol production from $CO_2$: In experiments using $CO_2$ bubbled through water at 50° C. using the integrated plasma catalysis technology system 100 and a $Cu_{0.2}Zn_{0.8}O$/$TiO_2$ NWs catalyst, the inventors observed a 4-6% $CO_2$ conversion without any methanol formation. These values are similar to literature reported values. $CO_2$ conversion decreased to ~1% when the catalyst was removed showing the slight extent of plasma catalysis synergy in this case. Compared to $CO_2$ conversions obtained with pure $CO_2$ splitting (13-27%), the inventors believe that the addition of water seems to suppress $CO_2$ conversion due to more favorable water gas shift reaction ($CO+H_2O \rightarrow CO_2+H_2$). Plasma flame quenching was also seen due to condensation of steam inside waveguide channels.

The addition of water for bi-reforming of methane ($CO_2$: $CH_4$:$H_2O$—1:1:1) showed 69% conversion even at low power input of 650 W with $H_2$/CO ratio close to 1. The addition of water for tri-reforming of methane ($CO_2$:$CH_4$: $H_2O$:$O_2$=0.4:1:0.75:0.2) showed a 40% conversion and syngas with $H_2$/CO ratio of 2 along with a methanol yield of 2%. The stability of the operation, i.e., plasma flame and the performance is fairly stable and reproducible when using water along with methane. In the case of tri-forming using methane and water along with $CO_2$, there is no need to control the catalyst temperature.

Methanol production is affected by catalyst used, power throughput (lpm/kW), and $H_2$/$CO_2$ ratio. The temperature of the catalyst bed also plays an important role in the selectivity of methanol versus CO. Using the equipment shown in FIG. 1, and the catalysts and reaction conditions shown in Table 4, greater than 57% $CO_2$ conversion was observed with a methanol production of 2.6%. In these experiments, the heat from plasma excited gas phase is directly integrated with catalyst bed and no control was provided. It is anticipated that the methanol yield can be improved by doing thermal management of the packed bed through heat exchange by using a water cooled jacket, by controlling the consistency of the catalyst bed temperature, and by using slightly higher reaction pressures.

TABLE 4

Rate of methanol production using different catalysts and process variables

| Catalyst | $H_2$/ $CO_2$ | $CO_2$ lpm/ kW | $CO_2$ conversion, % | Rate methanol production, mmol/kW · hr | Yield, % |
|---|---|---|---|---|---|
| $Cu_{0.1}Zn_{0.9}O$ | 2 | 6.8 | 44.4 | 437 | 2.4 |
| $Cu_{0.1}Zn_{0.9}O$ | 2 | 9.4 | 57.5 | 664 | 2.6 |
| $Cu_{0.1}Zn_{0.9}O$ | 3 | 4.6 | 57.1 | 327 | 2.7 |
| $Cu_{0.2}Zn_{0.8}O$ | 1 | 4.1 | 10.9 | 12 | 0.1 |
| $Cu_{0.2}Zn_{0.8}O$ | 2 | 5.7 | 47.9 | 204 | 1.3 |
| $Cu_{0.2}Zn_{0.8}O$ | 3.5 | 6.6 | 24.9 | 18 | 0.1 |
| $Cu_{0.2}Zn_{0.8}O$ | 5 | 3.5 | 44.6 | — | — |

As indicated in Table 5, using the present method, the $Cu_{0.1}Zn_{0.9}O$ catalysts show better performance than other catalysts. This could be due to more homogeneous bimetallic sites (Cu—Zn alloy) available for this catalyst. Also, using the present method, methanol yield and $CO_2$ conversion first increase and then decrease with increasing $CO_2$ lpm/kW. The inventors have found that $CO_2$ lpm/kW values between 5-10 produce the best results. Initially at very low flow rate, or low lpm/kW, the plasma discharge is not in complete synergy with the catalyst bed resulting in lower yields. But with increasing flow rates, plasma catalytic synergy is established, and methanol yield and $CO_2$ conversion peaks. Further, an increase in $CO_2$ flow rate decreases the gas ionization (due to low SEI) and decreases the residence time as well resulting in lower yields. The inventors have also found that the liquid production rate for the production of methanol is proportional to the catalyst bed temperature which in turn is related to $CO_2$ lpm/kW.

TABLE 5

Effect of plasma and process parameters on $CO_2$ conversion to methanol and CO

| Catalyst | Power, W | $H_2/CO_2$ | T bottom, °C. | T top, °C. | CO2 lpm/ kW | CO2 conversion | Methanol Yield, % | CO yield, % |
|---|---|---|---|---|---|---|---|---|
| $Cu_{0.1}Zn_{0.9}O$ | 450 | 3 | 375 | 290 | 7.3 | 43.7 | 1.5 | 42.2 |
| $Cu_{0.1}Zn_{0.9}O$ | 450 | 3 | 440 | 340 | 4.6 | 44 | 1.7 | 42.3 |
| $Cu_{0.1}Zn_{0.9}O$ | 450 | 3 | 245 | 130 | 4.7 | 24.2 | 1.4 | 22.8 |
| $Cu_{0.1}Zn_{0.9}O$ | 600 | 3 | 225 | 158 | 4.5 | 57.1 | 2.7 | 54.4 |
| $Cu_{0.1}Zn_{0.9}O$ | 500 | 2 | 285 | 170 | 6.8 | 44.4 | 2.4 | 42 |
| $Cu_{0.1}Zn_{0.9}O$ | 500 | 2 | 205 | 140 | 11.3 | 47.2 | 0 | 47.2 |
| $Cu_{0.1}Zn_{0.9}O$ | 700 | 2 | 280 | 190 | 9.4 | 57.5 | 2.6 | 54.9 |
| $Cu_{0.1}Zn_{0.9}O$ | 400 | 2 | 100 | 80 | 16.7 | 8.1 | 0.1 | 8 |
| $Cu_{0.2}Zn_{0.8}O$ | 450 | 3.5 | 160 | 130 | 6.6 | 24.9 | 0.1 | 24.8 |
| $Cu_{0.2}Zn_{0.8}O$ | 500 | 2 | 140 | 175 | 6.8 | 24.1 | 0.2 | 23.9 |
| $Cu_{0.2}Zn_{0.8}O$ | 550 | 2 | 305 | 145 | 5.7 | 47.9 | 1.3 | 46.6 |
| $Cu_{0.2}Zn_{0.8}O$ | 750 | 2 | 365 | 170 | 4.3 | 10.4 | 0.1 | 10.3 |
| $Cu_{0.2}Zn_{0.8}O$ | 600 | 2 | 265 | 160 | 10.5 | 11.2 | 0.1 | 11.1 |
| $Cu_{0.2}Zn_{0.8}O$ | 750 | 2 | 350 | 175 | 3.8 | 20.7 | 0.8 | 19.9 |
| $Cu_{0.2}Zn_{0.8}O$ | 750 | 1 | 260 | 120 | 4.1 | 10.9 | 0.1 | 10.8 |
| $Cu_{0.2}Zn_{0.8}O$ | 750 | 5.03 | 115 | 95 | 3.5 | 44.6 | 0 | 44.6 |

As indicated in Table 6, the inventive process of the integrated microwave plasma catalysis technology system and the copper-zinc catalyst have an energy efficiency for methanol production of about 660 mmol/kwh, which is at least 2 times higher than values reported by Wang et al. in 2018 using dielectric barrier discharge plasma technology. This results in an overall methanol production rate in mmol/hr that is over 100 times higher achieved with the DBD process.

TABLE 6

Comparison with literature reported DBD reactor

| Parameters | DBD Reactor[1] | Inventive Plasma unit |
|---|---|---|
| Catalyst | $Cu/Al_2O_3$ | $Cu_{0.1}Zn_{0.9}O$ |
| $H_2$ and $CO_2$ flow rates | 30 and 10 ml/min | 12 and 6 slpm |
| Power and time | 10 W, 1.5 hrs | 700 W, 1.5 hrs |
| Energy efficiency | 306 mmol/kwh | 664 mmol/kwh |
| Overall Methanol rate (mmol/hr) | 4.6 mmol/hr | 465 mmol/hr |

[1]Wang, L.; Yi, Y.; Guo, H.; Tu, X., *ACS Catalysis* 2018, 8 (1), 90-100

In summary, the present invention is an integrated microwave plasma (0.3-3 kw) catalytic reactor for distributed chemical production operating on the synergism of the catalyst and the microwave plasma at atmospheric pressures. In a preferred embodiment, the catalytic reactor is an adiabatic reactor in which all the heat generated by plasma excitation of molecules is transferred to the catalyst and no external heat is required making the process energy efficient. The reactor can be operated both in a packed bed mode and in a fluidized bed mode. The fluidized bed configuration allows the catalyst to come in contact with the plasma for a shorter time and is regenerated to achieve high selectivity and conversion. The reactor may be designed and constructed to operate continuously in synergy with the catalyst bed. In a preferred embodiment, the reactor system allows for high throughput processing of gases at 6-30 lpm/kW. The reactor can be used as part of a small scale GTL unit and the reaction pressures close to atmospheric pressure are significantly easier to manage and operate than the current thermal catalysis methods that require pressures in excess of 30 bar.

Further, the present invention is a method for using an alloyed bimetallic catalyst supported on a nanowire for plasma catalysis production. Without being bound by theory, it is believed that the fluidized catalyst and the plasma excited gas phase interact synergistically to effect the conversion of $CO_2$. Alloyed bimetallic catalysts have not been used in this type of application prior to the present invention.

The present invention is also a method to produce syngas employing microwave plasma reactor and catalyst bed. The syngas production method includes teaching alternative modes for introducing gases to the system. Additionally, the present invention is a method to produce methanol employing a microwave plasma reactor and a catalyst bed. The methanol production method includes teaching alternative modes for introducing gases to the system.

Unless defined otherwise, all technical and scientific terms used herein have the same meaning as commonly understood by one of ordinary skill in the art to which the presently disclosed subject matter pertains. Representative methods, devices, and materials are described herein, but are not intended to be limiting unless so noted.

The terms "a", "an", and "the" refer to "one or more" when used in the subject specification, including the claims. The term "ambient temperature" as used herein refers to an environmental temperature of from about 0° F. to about 120° F., inclusive.

Unless otherwise indicated, all numbers expressing quantities of components, conditions, and otherwise used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, or percentage can encompass variations of, in some embodiments ±20%, in some embodiments ±10%, in some embodiments ±5%, in some embodiments ±1%, in some embodiments ±0.5%, and in some embodiments to ±0.1%, from the specified amount, as such variations are appropriate in the disclosed application.

All compositional percentages used herein are presented on a "by weight" basis, unless designated otherwise.

The definitions and formulae used for determining the $CO_2$ conversion, CO selectivity, methanol yield, specific energy input (SEI) and energy efficiency are described below.

The conversion of $CO_2$ is defined as $$X_{CO2} = \frac{\text{moles of CO2 converted}}{\text{moles of initial CO2}} \times 100$$

Selectivity of CO is defined as $$S_{CO} = \frac{\text{moles of CO prodcued}}{\text{Moles of CO + methanol produced}} \times 100$$

Yield of methanol is defined as $$Y_{Methanol} = \frac{\text{moles of methanol prodcued}}{\text{moles of initial CO2}} \times 100$$

Specific energy input (SEI) is defined as plasma power applied divined by the gas flow rate.

$$SEI(Jcm^{-3}) = SEI(kJL^{-1}) = \frac{\text{power}(kW)}{\text{Flow rate}(Lmin^{-1})} \times 60$$

SEI is also expressed in electron volts per molecule and is related as follows:

SEI(ev per molecule)=0.254*SEI(kJL$^{-1}$)

Power throughput is defined as liter per minute of gases processed in plasma per kW of applied power and is represented as (liters per minute/kW). This is inversely proportional to the SEI and is measure of plasma processing capability:

Power throughput(lpm/kW)=60/(SEI(kJL$^{-1}$)

The energy efficiency is a measure of how efficiently the process performs compared to the standard reaction enthalpy, based on the specific energy input (SEI):

$$\eta = \frac{\chi_{Total} \times \Delta H^0_{298K}(kJmol^{-1})}{SEI(kJmol^{-1})} = \frac{\chi_{Total} \times \Delta H^0_{298K}(eV\ \text{molecule}^{-1})}{SEI(eV\ \text{molecule}^{-1})}$$

where η=energy efficiency and χ—total conversion and SEI is specific energy input. $\Delta H^0_{298K}$ is 283 kJ mol$^{-1}$ (or 2.93 eV per molecule) for pure $CO_2$ splitting.

The energy cost is the amount of energy consumed by the process (kJ per converted mol or eV per converted molecule):

$$EC(kJmol^{-1}_{conv}) = \frac{SEI(kJL^{-1}) \times 24.5(Lmol^{-1})}{\chi_{Total}}$$

Energy Efficiency of methanol formation (mmol/kWh) is defined as $$\text{energy efficiency} = \frac{\text{moles of methanol produced per hour}(mmol/hr)}{\text{discharge power}(kW)}$$

Yield for ammonia is defined as $$\text{Formation yield} = 100 \times \frac{\%\ NH_3(\text{plasma})}{2 \times \%\ N_2(\text{gas})}$$

It is understood that, in light of a reading of the foregoing description, those with ordinary skill in the art will be able to make changes and modifications to the present invention without departing from the spirit or scope of the invention, as defined herein.

What is claimed is:

1. A process to convert carbon dioxide in the presence of hydrogen gas into carbon monoxide plus water, synthesis gas, or methanol using an integrated plasma catalysis process comprising a microwave plasma discharge and an alloyed bimetallic nanowire catalyst wherein the plasma discharge fluidizes the catalyst before the carbon dioxide is fed into a reactor with the fluidized catalyst.

2. The process of claim 1 wherein the alloyed bimetallic nanowire catalyst is produced by plasma oxidation or by vacuum annealing of a bimetallic nanowire-based catalyst.

3. The process of claim 2 wherein the bimetallic nanowire-based catalyst is selected from the group consisting of (a) copper-zinc nanoparticles supported on titanium oxide nanowires ($Cu_xZn_{1-x}TiO_2$ NWs), (b) copper-zinc oxide nanowires (Cu—ZnO NWs), (c) copper supported on titanium oxide nanowires ($Cu_xTi_{1-x}O_2$), (d) nickel supported on titanium oxide nanowires ($Ni_xTi_{1-x}O_2$), and (e) copper-gallium supported on titanium oxide nanowires ($Cu_xGa_{1-x}O$—$TiO_2$ NWs).

4. The process of claim 1 wherein the process is performed at a pressure of less than 7 bar with the plasma power at from 3 lpm/kW to 30 lpm/kW.

5. The process of claim 1 wherein the process is performed in a reactor comprising a fixed catalyst bed or a fluidized catalyst bed, and a microwave plasma discharge source.

6. The process of claim 5 wherein the reactor has a throughput capacity of up to 30 Lpm/kW.

7. The process of claim 1 wherein the process is adiabatic and no external heat is supplied to the catalyst bed.

8. The process of claim 1 wherein the carbon dioxide is fed into the reactor through the fluidized catalyst before the hydrogen gas is fed into the reactor.

9. A process to convert carbon dioxide in the presence of hydrogen gas into carbon monoxide, synthesis gas, or methanol using an integrated plasma catalysis process comprising:
   (a) providing a reactor having a microwave plasma flame;
   (b) loading an alloyed bimetallic nanowire catalyst into the reactor such that the catalyst is fluidized by the plasma flame;
   (c) feeding the carbon dioxide into the reactor such that the carbon dioxide passes through the plasma flame and reacts with the fluidized catalyst to produce a first reaction product;
   (d) feeding the hydrogen gas into the reactor such that the hydrogen reacts with the first reaction product to produce carbon monoxide, synthesis gas, methanol, water, or a combination thereof; and,
   (g) collecting the carbon monoxide, synthesis gas, methanol, and water produced.

10. The process of claim 9 wherein the hydrogen gas is fed into the reactor after the plasma flame.

11. The process of claim 9 wherein the bimetallic nanowire-based catalysts are selected from the group consisting of (a) copper-zinc nanoparticles supported on titanium oxide nanowires ($Cu_xZn_{1-x}TiO_2$ NWs), (b) copper-zinc oxide nanowires (Cu—ZnO NWs), (c) copper supported on titanium oxide nanowires ($Cu_xTi_{1-x}O_2$), (d) nickel supported on titanium oxide nanowires ($Ni_xTi_{1-x}O_2$), and (e) copper-gallium supported on titanium oxide nanowires ($Cu_xGa_{1-x}O$—$TiO_2$ NWs).

12. The process of claim 9 wherein the reaction is performed at a pressure of less than 7 bar with the plasma power at from 3 lpm/kW to 30 lpm/kW.

13. The process of claim 9 wherein the process is adiabatic and no external heat is supplied to the catalyst bed.

14. A process to convert carbon dioxide in the presence of hydrogen gas into carbon monoxide plus water, synthesis gas, or methanol using an integrated plasma catalysis process, wherein the process is performed in a reactor comprising (a) a microwave plasma discharge source and (b) a fixed catalyst bed or a fluidized catalyst bed, and wherein the process comprises fluidizing an alloyed bimetallic nanowire catalyst with a microwave plasma discharge and then adding carbon dioxide and hydrogen gas to the fluidized catalyst.

15. The process of claim 14 wherein the alloyed bimetallic nanowire catalyst is produced by plasma oxidation or by vacuum annealing of a bimetallic nanowire-based catalyst.

16. The process of claim 15 wherein the bimetallic nanowire-based catalyst is selected from the group consisting of (a) copper-zinc nanoparticles supported on titanium oxide nanowires ($Cu_xZr_{1-x}TiO_2$ NWs), (b) copper-zinc oxide nanowires (Cu—ZnO NWs), (c) copper supported on titanium oxide nanowires ($Cu_xTi_{1-x}O_2$), (d) nickel supported on titanium oxide nanowires ($Ni_xTi_{1-x}O_2$), and (e) copper-gallium supported on titanium oxide nanowires ($Cu_xGa_{1-x}O$—$TiO_2$ NWs).

17. The process of claim 14 wherein the process is performed at a pressure of less than 7 bar with the plasma power at from 3 lpm/kW to 30 lpm/kW.

18. The process of claim 14 wherein the reactor has a throughput capacity of up to 30 Lpm/kW.

19. The process of claim 14 wherein the process is adiabatic and no external heat is supplied to the catalyst bed.

20. The process of claim 14 wherein the carbon dioxide is fed into the reactor through the fluidized catalyst before the hydrogen gas is fed into the reactor.

* * * * *